(12) United States Patent
Toth

(10) Patent No.: US 7,956,221 B2
(45) Date of Patent: Jun. 7, 2011

(54) PROCESS FOR DECOMPOSING CYCLOHEXYLHYDROPEROXIDE

(75) Inventor: Imre Toth, Geleen (NL)

(73) Assignee: DSM IP Assets B.V., Heerlen (NL)

(*) Notice: Subject to any disclaimer, the term of this patent is extended or adjusted under 35 U.S.C. 154(b) by 565 days.

(21) Appl. No.: 11/793,726

(22) PCT Filed: Dec. 16, 2005

(86) PCT No.: PCT/EP2005/013822
§ 371 (c)(1),
(2), (4) Date: Feb. 13, 2008

(87) PCT Pub. No.: WO2006/066904
PCT Pub. Date: Jun. 29, 2006

(65) Prior Publication Data
US 2010/0137645 A1 Jun. 3, 2010

(30) Foreign Application Priority Data

Dec. 22, 2004 (EP) .................................. 04078490

(51) Int. Cl.
*C07C 45/53* (2006.01)
*C07C 35/08* (2006.01)
(52) U.S. Cl. .................... 568/342; 568/357; 568/836
(58) Field of Classification Search .............. 568/342, 568/357, 836
See application file for complete search history.

(56) References Cited

U.S. PATENT DOCUMENTS 4,238,415 A * 12/1980 Bryan ........................... 568/342
5,824,819 A    10/1998 Dassel et al.
5,892,122 A     4/1999 Ostermaier et al.

FOREIGN PATENT DOCUMENTS

EP    0 092 867 A1    11/1983
GB         716820     10/1954

OTHER PUBLICATIONS

International Preliminary Search Report mailed May 8, 2006 in PCT/EP2005/013822.
Written Opinion mailed May 8, 2006 in PCT/EP2005/013822.
International Preliminary Report on Patentability mailed Mar. 29, 2007 in PCT/EP2005/013822.
Tolman et al., *Journal of Molecular Catalysis* 48 (1988) 129-148.
Hofmann et al, "Über die Zersetzung organischer Hydroperoxide in Gegenwart von Basen", Journal für prakitsche Chemie. 4. Reihe. Band 37. pp. 102-109 (1968) (Native language and full text English-language translation).

* cited by examiner

*Primary Examiner* — Sikarl A Witherspoon
(74) *Attorney, Agent, or Firm* — Nixon & Vanderhye P.C.

(57) ABSTRACT

The present invention relates to a process for decomposing cyclohexylhydroperoxide into cyclohexanone, said process comprising mixing an organic feed solution comprising cyclohexylhydroperoxide with an aqueous base solution in the absence of a transition metal catalyst resulting in a mixture comprising (i) an aqueous phase and (ii) an organic phase comprising cyclohexanone and cyclohexanol.

13 Claims, No Drawings

PROCESS FOR DECOMPOSING CYCLOHEXYLHYDROPEROXIDE

This application is the US national phase of international application PCT/EP2005/013822 filed 16 Dec. 2005 which designated the U.S. and claims benefit of EP 04078490.2, dated 22 Dec. 2004, the entire content of which is hereby incorporated by reference.

The present invention relates to a process for decomposing cyclohexylhydroperoxide into cyclohexanone.

Cyclohexanone may be used for the production of caprolactam and/or adipic acid, both nylon intermediates. For caprolactam and adipic acid production, a known route for cyclohexanone production involves oxidation of cyclohexane to yield a mixture containing cyclohexane, cyclohexanone, cyclohexanol, cyclohexylhydroperoxide and by-products. For the production of caprolactam, cyclohexanone is the desired intermediate. For this purpose, cyclohexylhydroperoxide can first be converted to cyclohexanone and cyclohexanol and the cyclohexanol can be converted to cyclohexanone in a separate step.

Document EP-A-092867 describes a process wherein an organic feed solution comprising cyclohexylhydroperoxide is treated with a transition metal salt like cobalt sulphate or chromium nitrate in the presence of an aqueous solution of an alkali metal hydroxide at a temperature of 70-115° C. to obtain a mixture containing an organic phase comprising cyclohexanone and cyclohexanol and an aqueous phase. EP-A-09.2867 describes that effecting such a transition metal catalyzed, two-phase decomposition at temperatures of 70-115° C. results in improved selectivity to cyclohexanone and cyclohexanol compared with effecting such decomposition at higher temperatures. In such low temperature, two-phase decomposition processes, the molar ratio of cyclohexanone formed to cyclohexanol formed in the organic phase is usually at most 1.5.

It has now surprisingly been found that the molar ratio of cyclohexanone to cyclohexanol obtained in the decomposition reaction of cyclohexylhydroperoxide (hereinafter referred to as molar ratio of cyclohexanone formed to cyclohexanol formed) is markedly increased by effecting the decomposition of cyclohexylhydroperoxide in the presence of an aqueous base solution, but in the absence of a transition metal catalyst. An increased molar ratio of cyclohexanone formed to cyclohexanol formed is advantageous in case for example caprolactam is the ultimate desired product because for the production of caprolactam cyclohexanone is the desired intermediate. In case for example caprolactam is the ultimate desired product, an increased molar ratio of cyclohexanone formed to cyclohexanol formed is advantageous because less cyclohexanol needs to be isolated from the mixture obtained after decomposition and less cyclohexanol needs to be converted to cyclohexanone. Thus the cyclohexanone recovery and purification can be carried out easier.

Accordingly, the invention provides a process for decomposing cyclohexylhydroperoxide into cyclohexanone, said process comprising mixing an organic feed solution comprising cyclohexylhydroperoxide with an aqueous base solution in the absence of a transition metal catalyst resulting in a mixture comprising (i) an aqueous phase and (ii) an organic phase comprising cyclohexanone and cyclohexanol.

It has surprisingly been found that with the process of the invention a molar ratio of cyclohexanone formed to cyclohexanol formed in the organic phase comprising cyclohexanone and cyclohexanol higher than 2, even a molar ratio higher than 2.5 or even a molar ratio higher than 3 can be obtained. As used herein, the molar ratio of cyclohexanone formed to cyclohexanol formed in the organic phase is defined as $n_{anone\ formed}/n_{anol\ formed}$, wherein $n_{anone\ formed}$=concentration of cyclohexanone in the organic phase minus concentration of cyclohexanone in the organic feed solution and $n_{anol\ formed}$=concentration of cyclohexanol in the organic phase minus concentration of cyclohexanol in the organic feed solution. All concentrations are in mol per kg.

Therefore, the invention further provides a process for decomposing cyclohexylhydroperoxide into cyclohexanone, said process comprising mixing an organic feed solution comprising cyclohexylhydroperoxide with an aqueous base solution in the absence of a transition metal catalyst resulting in a mixture containing (i) an aqueous phase and (ii) an organic phase comprising cyclohexanone and cyclohexanol, wherein the molar ratio of cyclohexanone formed to cyclohexanol formed in the organic phase is higher than 2. Preferably, this molar ratio is higher than 2.5 and even more preferably it is higher than 3.

A further advantage of the process according to the invention is that, compared with a process as for example described in EP-A-092867 a higher selectivity of the decomposition of cyclohexylhydroperoxide into cyclohexanone and cyclohexanol can be obtained. It has surprisingly been found that this high selectivity can even be maintained at increased temperatures. This was unexpected since the prior art relating to cyclohexylhydroperoxide decomposition in the presence of an aqueous base solution and a transition metal catalyst teaches that increased temperature results in decreased selectivity. An additional advantage of the process according to the invention is that the base consumption can be reduced.

In the process of the present invention, decomposing cyclohexylhydroperoxide present in the organic feed solution is effected in the absence of a transition metal catalyst. This is done by mixing the organic feed solution comprising cyclohexylhydroperoxide with the aqueous base solution in the absence of a transition metal catalyst. As used herein, effecting the decomposition in the absence of a transition metal catalyst implies that no transition metal compound is purposely added to the mixture to be decomposed in an amount that notably catalyzes the decomposition. Alternatively, transition metal catalyst present in the organic feed solution is removed and/or deactivated before the organic feed solution enters the decomposition section to such an extent that there is no catalytic activity in the decomposition. Examples of transition metal compounds that notably catalyses the decomposition, even when present at small concentrations, are Cr salts and especially Co salts. Therefore, the process of the present invention especially relates to effecting the decomposition without purposely adding a Co and/or Cr catalyst to the process of decomposing cyclohexylhydroperoxide. In the framework of this invention, the entering of transition metal compounds into the mixture that is subjected to decomposition, due to corrosion of the reactor wall, is, however, not considered as purposely adding a transition metal compound to the mixture that is subjected to decomposition.

The cyclohexylhydroperoxide, which is decomposed in the process of the invention, can be obtained with various known processes.

Preferably, preparing the cyclohexylhydroperoxide involves oxidizing cyclohexane with an oxygen containing gas in the absence of substances promoting the decomposition of the cyclohexylhydroperoxide formed (hereinafter referred to as uncatalyzed oxidation) resulting in an oxidation reaction mixture comprising cyclohexane, cyclohexanone, cyclohexanol, cyclohexylhydroperoxide, acids, esters, low boiling compounds, and high boiling compounds. With low boiling compounds is meant organic compounds having a boiling point lower than cyclohexanone and higher than cyclohexane. Examples are 1-butanol, 1-pentanal, 1-hexanal, 1-pentanol and epoxy-cyclohexane. With high boiling compounds is meant organic compounds having a boiling point higher than cyclohexanol. Examples are 2-cyclohexylidene cyclohexanone, 2-hexylidene cyclohexanone and 2-(cyclohexen-1-yl)cyclohexanone. The oxidation usually takes place in the liquid phase. As oxygen-containing gas use can be made for instance of pure oxygen, air, rich or poor in oxygen, or oxygen mixed with nitrogen or another inert gas. Suitable oxidation temperatures are between 120 and 200° C. Preferably, an oxidation temperature between 140 and 190° C. is used. Compared with the process as for example described in EP-A-92867, the process according to the invention has the advantage that the difference between the oxidation temperature and the decomposition temperature can be decreased. This is advantageous with respect to energy consumption as for example the degree of cooling of the reaction mixture leaving the oxidation reactor before allowing the cyclohexylhydroperoxide to decompose can be reduced. The oxidation reaction is usually carried out for 5 minutes to 24 hours. The pressure is usually between 0.1 and 5 MPa, preferably between 0.2 and 2.5 MPa. Uncatalyzed cyclohexane oxidation is preferred to catalyzed cyclohexane oxidation because uncatalyzed cyclohexane oxidation results in higher yields of cyclohexylhydroperoxide and because there is no need to separate and/or deactivate the transition metal oxidation catalyst before decomposing the cyclohexylhydroperoxide with the process according to the invention. As a rule, the reaction mixture obtained in such uncatalyzed cyclohexane oxidation comprises a weight percentage of cyclohexylhydroperoxide that is at least comparable to the weight percentages of cyclohexanone and cyclohexanol. Often, the amount of cyclohexylhydroperoxide in the reaction mixture obtained in such uncatalyzed cyclohexane oxidation is at least two times as large as the amount of cyclohexanone and cyclohexanol.

Optionally, prior to subjecting the cyclohexylhydroperoxide, present in a reaction mixture obtained by oxidation of cyclohexane with an oxygen-containing gas, to a decomposition process according to the invention, the reaction mixture obtained by oxidation of cyclohexane with an oxygen-containing gas can be concentrated by separating, preferably by flashing or distilling, all or preferably part of the cyclohexane. Optionally, prior to decomposing cyclohexylhydroperoxide, obtained by oxidation of cyclohexane, according to the invention and preferably after said concentrating (if applied), the oxidation reaction mixture may be treated with water or preferably with an aqueous alkaline solution, as for example described in EP-A-4105, for the purpose of neutralizing acids formed in the oxidation. When applying such a neutralisation, the total base consumption can be reduced by applying in the neutralisation at least a part of the aqueous phase that can be separated off from the reaction mixture after the decomposing.

The cyclohexylhydroperoxide to be decomposed according to the invention may be present in any organic feed solution. The cyclohexylhydroperoxide concentration in the organic feed solution is not critical. The cyclohexylhydroperoxide may for example be present in an organic feed solution comprising between 0.1 and 20 wt. % cyclohexylhydroperoxide (relative to the organic feed solution). In case the process according to the invention is applied for decomposing cyclohexylhydroperoxide obtained by oxidizing cyclohexane, the organic feed solution comprising cyclohexylhydroperoxide usually also comprises other compounds, for example (1) cyclohexane and/or (2) cyclohexanone and/or (3) cyclohexanol. The sum concentration of cyclohexanone and cyclohexanol in the organic feed solution is not critical and is for instance between 0 and 20 wt. % (relative to the total organic feed solution).

It has further been found that in particular the temperature at which the mixing is effected, the pH of the aqueous phase, the volume ratio of the aqueous phase to the organic phase and the concentration of carboxylic acid salts in the aqueous base solution may further influence the molar ratio of cyclohexanone formed to cyclohexanol formed in the organic phase.

Preferably, said mixing is effected at a temperature higher than 70° C., more preferably higher than 80° C., more preferably higher than 90° C. and even more preferably higher than 100° C. Increasing the temperature results in an increase of the decomposition reaction velocity and hence lower residence times. It has surprisingly been found that increasing the temperature does not significantly impair the molar ratio of cyclohexanone formed to cyclohexanol formed in the organic phase and the selectivity of the decomposition of cyclohexylhydroperoxide into cyclohexanone and cyclohexanol. In case the cyclohexylhydroperoxide to be decomposed with the process of the invention is obtained by oxidizing cyclohexane, effecting said mixing at increased temperatures is in particular advantageous, in particular with respect to reduction of energy consumption, because at increased decomposition temperatures the degree of cooling of the reaction mixture leaving the oxidation reactor before allowing the cyclohexylhydroperoxide to decompose can be reduced. Preferably, said mixing is effected at a temperature lower than 170° C., more preferably lower than 160° C. and even more preferably lower than 150° C. It has been found that effecting the decomposing at a temperature higher than 160° C. may result in a decrease of the molar ratio of cyclohexanone formed to cyclohexanol formed in the organic phase and may result in a decrease of the selectivity of the decomposition of cyclohexylhydroperoxide into cyclohexanone and cyclohexanol. This decrease may even be more pronounced when the mixing is effected at a temperature higher than 170° C.

The mixing is preferably effected with such a quantity of aqueous base solution that the pH of aqueous phase is higher than 9, measured at 25° C. The pH of the aqueous phase is preferably higher than 10, more preferably higher than 11, more preferably higher than 12, more preferably higher than 13 and even more preferably higher than 13.5, measured at 25° C. By increasing the pH of the aqueous phase, the decomposition reaction velocity is increased. By increasing the pH of the aqueous phase, the molar ratio of cyclohexanone formed to cyclohexanol formed in the organic phase may be further increased. Additionally, an increased pH of the aqueous phase may result in an increased selectivity of the decomposition reaction to cyclohexanone and cyclohexanol. On the other hand, an increased pH of the aqueous phase results in an increased base consumption. In case the cyclohexylhydroperoxide to be decomposed with the process of the invention is obtained by oxidizing cyclohexane, the mixing is advantageously effected at high temperature and relatively high pH of the aqueous phase, because this results in a high selectivity to cyclohexanone and cyclohexanol and in a high molar ratio of cyclohexanone formed to cyclohexanol formed and at the same time in decreased energy consumption.

In the process of the invention, the volume ratio of the aqueous phase to the organic phase is preferably higher than 0.02, more preferably higher than 0.1 and even more preferably higher than 0.15. Increasing the volume ratio of the aqueous phase to the organic phase results in increased decomposition reaction velocity. It has also been found that increasing the volume ratio of the aqueous phase to the organic phase may result in an increased selectivity of the decomposition of cyclohexylhydroperoxide into cyclohexanone and cyclohexanol and in an increased molar ratio of cyclohexanone formed to cyclohexanol formed in the organic phase. There is no specific upper limit for the volume ratio of the aqueous phase to the organic phase. From an economical point of view, however, the volume ratio of the aqueous phase to the organic phase is preferably lower than 5.

The pressure, at which mixing the organic feed solution comprising cyclohexylhydroperoxide with the aqueous base solution is effected, is not critical and may be varied within wide ranges. The pressure employed is for example between 0.1 and 5 MPa and advantageously depends on the temperature used.

The process of the invention involves mixing the organic feed solution comprising cyclohexylhydroperoxide with the aqueous base solution. The aqueous base solution may be added to the organic feed solution in any suitable manner. Mixing the organic feed solution with the aqueous base solution may be effected by any suitable method, for example by using a packed column, a flow or line mixer, a pump, a static mixer, an agitated vessel or combinations thereof. Mixing may also involve injecting the organic feed solution into the aqueous base solution, or vice versa.

As used herein, an aqueous base solution refers to an aqueous solution comprising dissolved base(s). Preferably, the base is an earth alkali metal hydroxide and/or one or more salts of an earth alkali metal or the base is an alkali metal hydroxide and/or one or more salts of an alkali metal. Hence, preferably, the aqueous base solution is an aqueous solution comprising an earth alkali metal hydroxide and/or one or more salts of an earth alkali metal or the aqueous base solution is an aqueous solution comprising an alkali metal hydroxide and/or one or more salts of an alkali metal. More preferably, the aqueous base solution is an aqueous solution comprising an alkali metal hydroxide and/or one or more salts of an alkali metal. Suitable (earth) alkali metal salts are (earth) alkali metal phosphates, (earth) alkali metal carbonates and (earth) alkali metal bicarbonates. Preferred (earth) alkali metal salts are (earth) alkali metal carbonates and (earth) alkali metal bicarbonates. A preferred earth alkali metal is magnesium. The alkali metal is preferably potassium or sodium, more preferably sodium. In a preferred embodiment, the aqueous base solution further comprises carboxylic acids salts. It has been found that the presence of carboxylic acid salts results in an increased reaction velocity for decomposing cyclohexylhydroperoxide into the desired products cyclohexanone and cyclohexanol. It has further been found that the presence of carboxylic acid salts may result in an increased molar ratio of cyclohexanone formed to cyclohexanol formed in the organic phase. Salts of mono- and polycarboxylic acids in which the carboxylic acid moiety preferably comprises 1-24 C-atoms are suitable, more preferably the carboxylic acid moiety comprises 1-12 C-atoms. Examples of suitable carboxylic acids in the salts are formic acid, acetic acid, propionic acid, butyric acid, adipic acid, hexanoic acid, heptanoic acid, pentanoic acid, propane dicarboxylic acid, glutaric acid, hexane dicarboxylic acid, heptane dicarboxylic acid, stearic acid and decanoic acid. Special preference is given to the use of mixtures of different carboxylic acids, since these are simply obtainable. Preferably, the carboxylic acid salts concentration in the aqueous base solution is higher than 5 wt. %, more preferably higher than 10 wt. %. Preferably, the carboxylic acid salts concentration in the aqueous base solution is lower than the solubility limit of the carboxylic acid salts in the aqueous base solution at the applied reaction conditions.

The reaction mixture obtained in the decomposition of cyclohexylhydroperoxide can be processed further by separating off the aqueous phase and subjecting the organic phase, if so desired after washing with water, to distilling for recovering cyclohexanone. Therefore, the process of the invention further comprises separating the aqueous phase from the organic phase. Said separating may be effected by any suitable method, for example decantation and/or making use of plate separators.

The process of the invention preferably further comprises reusing a portion of the separated aqueous phase in the decomposition reaction. In that case, the aqueous base solution comprises a portion of the aqueous phase obtained after said separating. The aqueous base solution will then already contain carboxylic acid salts as mentioned above. The carboxylic acids can be formed as by-product in the oxidation and/or decomposition, upon which owing to the presence of (earth) alkali metal, salts are formed with the carboxylic acids.

The process of the invention preferably further comprises distilling the organic phase, obtained after said separating, to obtain cyclohexanone.

In a preferred embodiment, the present invention provides a process for the preparation of cyclohexanone, said process comprising
(a) Oxidizing cyclohexane with an oxygen-containing gas in the absence of a transition metal catalyst to obtain an oxidation reaction mixture comprising cyclohexylhydroperoxide, cyclohexane, cyclohexanol, cyclohexanone, acids, esters, low boiling compounds and high boiling compounds;
(b) Optionally, separating part of the cyclohexane from said oxidation reaction mixture;
(c) Optionally, neutralizing acids formed in the oxidation by treating the oxidation reaction mixture with water or preferably with an aqueous base solution;
(d) Decomposing cyclohexylhydroperoxide obtained in (a) with the process according to the invention to obtain a mixture comprising (i) an aqueous phase and (ii) an organic phase comprising cyclohexane, cyclohexanone, cyclohexanol, low boiling compounds and high boiling compounds;
(e) Separating the aqueous phase from the organic phase;
(f) Optionally, recycling a portion of the separated aqueous phase to (c);
(g) Distilling the organic phase to obtain cyclohexanone.

In this preferred embodiment, distilling the organic phase to obtain cyclohexanone preferably comprises the following steps: separating cyclohexane from the organic phase (g.1), separating low boiling compounds from the organic phase (g.2), separating cyclohexanone from the organic phase (g.3) and separating cyclohexanol from the organic phase (g.4). Other purification and/or recovery steps may be carried out between (g.1), (g.2), (g.3) and/or (g.4). More preferably, in this preferred embodiment, distilling the organic phase to obtain cyclohexanone comprises separating, by distillation, cyclohexane from the organic phase to obtain a top product comprising cyclohexane and a first bottom product comprising cyclohexanone, cyclohexanol, low boiling compounds and high boiling compounds;

separating, by distillation, low boiling compounds from the first bottom product to obtain a top product comprising low boiling compounds and a second bottom product comprising cyclohexanone, cyclohexanol and high boiling compounds; and separating, by distillation, cyclohexanone from the second bottom product to obtain a top product comprising cyclohexanone and a third bottom product comprising cyclohexanol and high boiling compounds; and separating, by distillation, cyclohexanol from the third bottom product to obtain a top product comprising cyclohexanol and a bottom product comprising high boiling compounds. Cyclohexanol may subsequently be subjected to a dehydrogenation reaction. Other purification and/or recovery steps may be carried out between the above mentioned distillation steps.

The invention will be elucidated by the following examples without being limited thereto.

The conversion is calculated by dividing the amount of cyclohexylhydroperoxide converted during the decomposition by the initial amount of cyclohexylhydroperoxide (amount in mols). The selectivity for cyclohexanone and cyclohexanol is calculated by dividing the sum of the cyclohexanone and cyclohexanol formed during the decomposition of cyclohexylhydroperoxide by the amount of cyclohexylhydroperoxide converted during the decomposition (amounts in mols).

COMPARATIVE EXPERIMENT A 0.816 g of $Na_2CO_3$ and 0.413 g of NaOH were dissolved in 9.056 g of a degassed aqueous solution of 1.25 g of sodium heptanoate and 0.34 g of disodium heptadionate with stirring at room temperature under an atmosphere of $N_2$. The obtained clear solution was transferred into a 150 ml Parr autoclave (made of Hastelloy C) under a gentle stream of $N_2$. The autoclave was pressurized then to 0.5 MPa with $N_2$; then heating and stirring were started. When the temperature reached 65° C. in the autoclave, feeding of a degassed aqueous solution of $CoSO_4$ containing 100 ppm of cobalt was started into the reactor by using a Gilson pump while the reactor was further heated to 80° C. After 1 minute of feeding (1 ml/min), the cobalt feed was decreased to 0.033 ml/min until the end of the experiment. When the temperature reached 80° C., 51.66 g of a cyclohexane oxidate solution was injected into the reactor from a sample cylinder (kept at room temperature) by using 2 MPa $N_2$ pressure. The cyclohexane oxidate solution contained 12.034 mmol of cyclohexylhydroperoxide, 3.678 mmol of cyclohexanol, 2.115 mmol of cyclohexanone, 0.648 mmol of C1-C6 mono and dicarboxylic acids, 0.037 mmol of cyclohexyl esters of C1-C6 mono and dicarboxylic acids and 0.937 mmol of various non-acidic organic oxo-compounds as determined by a calibrated GC method. After injection of the cyclohexane oxidate solution, 80° C. was maintained in the reactor for 30 minutes. Then feeding of the cobalt solution was stopped and the reactor was cooled back immediately by replacing the heating mantle with an ice bath. After about 20-30 minutes standing, the ice bath was removed; the reactor was slowly depressurized and opened. The contents of the autoclave were weighed back after transferring into an Erlenmeyer flask. A sample was taken immediately from the colorless hazy organic phase for GC analysis. The clear brow-yellow aqueous phase was then separated and weighed back. A known portion of the aqueous phase was taken then for acidification to pH 1. The acidification was carried out by the drop-wise addition of cc. HCl to the aqueous solution using a pH electrode and stirring. The obtained light yellow aqueous emulsion was then extracted 4 times with similar volume aliquots of diethyl ether. The ether extracts were united and weighed back. Then a sample was taken from the united extract for GC analysis. After evaluating the calibrated GC spectra of the organic phase and ether extract a mass balance was established by adding up the two fractions. This showed the following amount of components present: 0.146 mmol of cyclohexylhydroperoxide, 7.997 mmol of cyclohexanol, 8.546 mmol of cyclohexanone, 0.991 mmol of C1-C6 mono and dicarboxylic acids, no cyclohexyl esters of C1-C6 mono and dicarboxylic acids and 1.305 mmol of various non-acidic organic oxo-compounds. This corresponds to 98.8% of conversion of cyclohexylperoxide with 90.1% selectivity to newly formed cyclohexanone and cyclohexanol with a molar ratio of 1.50. Cyclohexanol and acids formed by the hydrolysis of the esters were considered as components already present in the starting mixture. The selectivity to acids and undetected components was 2.6 and 4.2%, respectively. The undetected components consist mostly of $CO_2$, as determined authentically in similar experiments by using isotopic $Na_2^{13}CO_3$ instead of $Na_2^{12}CO_3$ in the starting base mixture and determining $Na_2^{12}CO_3/.Na_2^{13}CO_3$ ratio after the reaction by mass spectroscopy. Neutralization of the formed acids and $CO_2$ results in the consumption of an equivalent amount of base. The results are summarized in Table 1.

EXAMPLE 1

Comparative Experiment A was repeated by using an aqueous base solution containing 0.823 g $Na_2CO_3$ and 0.366 g of NaOH in 9.03 g of a degassed aqueous solution of 1.25 g of sodium heptanoate and 0.34 g of disodium heptadionate. In contrast to Comparative Experiment A, this experiment was carried out in the absence of cobalt, i.e. no cobalt was added. Furthermore, an amount of 52.74 g of a cyclohexane oxidate solution was used for injection in this experiment. The oxidate solution contained 12.352 mmol of cyclohexylhydroperoxide, 3.979 mmol of cyclohexanol, 2.331 mmol of cyclohexanone, 0.636 mmol of C1-C6 mono and dicarboxylic acids, 0.040 mmol of cyclohexyl esters of C1-C6 mono and dicarboxylic acids and 1.081 mmol of various non-acidic organic oxo-compounds. The reaction was carried out in the absence of cobalt at 80° C. for 30 minutes similarly as described above in Comparative Experiment A. After the reaction the following amount of components were found back in the two product fractions: 5.707 mmol of cyclohexylhydroperoxide, 5.829 mmol of cyclohexanol, 6.871 mmol of cyclohexanone, 0.720 mmol of C1-C6 mono and dicarboxylic acids, no cyclohexyl esters of C1-C6 mono and dicarboxylic acids and 1.298 mmol of various non-acidic organic oxo-compounds. This corresponds to 53.8% of conversion of cyclohexylperoxide with 95.6% selectivity to newly formed cyclohexanone and cyclohexanol with a molar ratio of 2.51. The selectivity to acids and undetected components was 0.7% and 0.5%, respectively. The example shows that the selectivity to cyclohexanone/cyclohexanol and the molar ratio of cyclohexanone to cyclohexanol is significantly higher and less base is consumed (as a consequence of the lower selectivity to acids and $CO_2$) in the absence of cobalt than in the presence of cobalt (Comparative Experiment A). The results are summarized in Table 1.

EXAMPLE 2

Example 1 was repeated by using no sodium heptanoate and disodium heptadionate in the aqueous base solution, which contained 0.868 g $Na_2CO_3$ and 0.378 g of NaOH in 9.05 g of a degassed water. Furthermore, an amount of 52.87 g of cyclohexane oxidate solution used for injection in this experiment. The oxidate solution contained 12.423 mmol of cyclohexylhydroperoxide, 3.720 mmol of cyclohexanol, 2.196 mmol of cyclohexanone, 0.658 mmol of C1-C6 mono and dicarboxylic acids, 0.038 mmol of cyclohexyl esters of C1-C6 mono and dicarboxylic acids and 0.870 mmol of various non-acidic organic oxo-compounds. The reaction was carried in the absence of cobalt at 80° C. for 30 minutes similarly as described above in Comparative Experiment A.

After the reaction the following amount of components were found back in the two product fractions: 6.653 mmol of cyclohexylhydroperoxide, 5.596 mmol of cyclohexanol, 5.940 mmol of cyclohexanone, 0.766 mmol of C1-C6 mono and dicarboxylic acids, no cyclohexyl esters of C1-C6 mono and dicarboxylic acids and 0.952 mmol of various non-acidic organic oxo-compounds. This corresponds to 46.5% of conversion of cyclohexylperoxide with 96.7% selectivity to newly formed cyclohexanone and cyclohexanol with a molar ratio of 2.04. The selectivity to acids and undetected components was 1.2% and 0.6%. The example shows that the selectivity to cyclohexanone/cyclohexanol, the molar ratio of cyclohexanone to cyclohexanol is significantly higher and less base is consumed in the absence of cobalt than in Comparative Experiment A. The results are summarized in Table 1.

EXAMPLE 3

Example 1 was repeated by using significantly more aqueous phase for the reaction. Thus, instead of the amounts given in Example 1, 2.66 g of $Na_2CO_3$ and 1.41 g of NaOH were dissolved in 35.8 g of a degassed aqueous solution containing 4.97 g of sodium heptanoate and 1.344 g of disodium heptadionate. Furthermore, an amount of 41.97 g of a cyclohexane oxidate solution was used for injection in this experiment. The oxidate solution contained 9.450 mmol of cyclohexylhydroperoxide, 2.788 mmol of cyclohexanol, 1.659 mmol of cyclohexanone, 0.503 mmol of C1-C6 mono and dicarboxylic acids, 0.029 mmol of cyclohexyl esters of C1-C6 mono and dicarboxylic acids and 0.676 mmol of various non-acidic organic oxo-compounds. The reaction was carried in the absence of cobalt at 80° C. for 30 minutes similarly as described above in Comparative Experiment A. After the reaction the following amount of components were found back in the two product fractions: 0.054 mmol of cyclohexylhydroperoxide, 4.440 mmol of cyclohexanol, 9.005 mmol of cyclohexanone, 0.588 mmol of C1-C6 mono and dicarboxylic acids, no cyclohexyl esters of C1-C6 mono and dicarboxylic acids and 0.967 mmol of various non-acidic organic oxo-compounds. This corresponds to 99.4% of conversion of cyclohexylperoxide with 95.5% selectivity to newly formed cyclohexanone and cyclohexanol with a molar ratio of 4.53. The selectivity to acids and undetected components was 0.6% and 0.9%, respectively. The example shows that the selectivity to cyclohexanone/cyclohexanol and the molar ratio of cyclohexanone to cyclohexanol can be further increased by increasing the volume of the aqueous phase as compared to Example 1. The results are summarized in Table 1.

EXAMPLE 4

Example 2 was repeated except that 120° C. reaction temperature was used with significantly more aqueous phase. Thus instead of the amounts given in Example 2, 3.27 g of $Na_2CO_3$ and 1.39 g of NaOH were dissolved in 36.11 g of degassed water. Furthermore, an amount of 38.00 g of a cyclohexane oxidate solution was used for injection in this experiment. The oxidate solution contained 8.488 mmol of cyclohexylhydroperoxide, 2.660 mmol of cyclohexanol, 1.532 mmol of cyclohexanone, 0.450 mmol of C1-C6 mono and dicarboxylic acids, 0.026 mmol of cyclohexyl esters of C1-C6 mono and dicarboxylic acids and 0.660 mmol of various non-acidic organic oxo-compounds. The reaction was carried in the absence of cobalt at 120° C. for 10 minutes similarly as described above in Comparative Experiment A. After the reaction the following amount of components were found back in the two product fractions: 0.048 mmol of cyclohexylhydroperoxide, 4.219 mmol of cyclohexanol, 8.060 mmol of cyclohexanone, 0.600 mmol of C1-C6 mono and dicarboxylic acids, no cyclohexyl esters of C1-C6 mono and dicarboxylic acids and 0.887 mmol of various non-acidic organic oxo-compounds. This corresponds to 99.4% of conversion of cyclohexylperoxide with 95.5% selectivity to newly formed cyclohexanone and cyclohexanol with a molar ratio of 4.26. The selectivity to acids and undetected components was 1.5% and 0.5%, respectively. The example shows that the rate of decomposition and the molar ratio of cyclohexanone to cyclohexanol can be increased while maintaining high selectivity by increasing the temperature and volume ratio of the aqueous phase to the organic phase as compared to Example 2. The results are summarized in Table 1.

EXAMPLE 5

Example 4 was repeated except that only $Na_2CO_3$ was used in the aqueous phase. Thus, 4.0 g of $Na_2CO_3$ was dissolved in 41.38 g of degassed water.

Furthermore, an amount of 37.52 g of a cyclohexane oxidate solution was used for injection in this experiment. The oxidate solution contained 10.628 mmol of cyclohexylhydroperoxide, 2.034 mmol of cyclohexanol, 1.495 mmol of cyclohexanone, 0.290 mmol of C1-C6 mono and dicarboxylic acids, 0.015 mmol of cyclohexyl esters of C1-C6 mono and dicarboxylic acids and 0.240 mmol of various non-acidic organic oxo-compounds. Otherwise, the reaction was carried in the absence of cobalt at 120° C. for 20 minutes similarly as described above in Comparative Experiment A. After the reaction the following amount of components were found back in the two product fractions: 1.509 mmol of cyclohexylhydroperoxide, 4.393 mmol of cyclohexanol, 7.645 mmol of cyclohexanone, 0.619 mmol of C1-C6 mono and dicarboxylic acids, no cyclohexyl esters of C1-C6 mono and dicarboxylic acids and 0.297 mmol of various non-acidic organic oxo-compounds. This corresponds to 85.8% of conversion of cyclohexylperoxide with 93.1% selectivity to newly formed cyclohexanone and cyclohexanol with a molar ratio of 2.62. The selectivity to acids and undetected components was 3.4% and 2.8%, respectively. The example shows that $Na_2CO_3$ can be used alone in the aqueous base solution advantageously as compared to Comparative Experiment A. The results are summarized in Table 1.

EXAMPLE 6

Example 5 was repeated except that only NaOH was used in the aqueous phase. Thus, 4.04 g of NaOH was dissolved in 40.03 g of degassed water. Furthermore, an amount of 40.85 g of a cyclohexane oxidate solution was used for injection in this experiment. The oxidate solution contained 11.334 mmol of cyclohexylhydroperoxide, 2.140 mmol of cyclohexanol, 1.789 mmol of cyclohexanone, 0.283 mmol of C1-C6 mono and dicarboxylic acids 0.018 mmol of cyclohexyl esters of C1-C6 mono and dicarboxylic acids and 0.416 mmol of various non-acidic organic oxo-compounds. Otherwise, the reaction was carried in the absence of cobalt at 120° C. for 20 minutes similarly as described above in Comparative Experiment A. After the reaction the following amount of components were found back in the two product fractions: 0.033 mmol of cyclohexylhydroperoxide, 4.639 mmol of cyclohexanol, 10.225 mmol of cyclohexanone, 0.468 mmol of C1-C6 mono and dicarboxylic acids, no cyclohexyl esters of C1-C6 mono and dicarboxylic acids and 0.562 mmol of various non-acidic organic oxo-compounds. This corresponds to a 99.7% of conversion of cyclohexylperoxide with 96.6% selectivity to newly formed cyclohexanone and cyclohexanol with a molar ratio of 3.40. The selectivity to acids and undetected components was 1.5% and 0.5%, respectively. The example shows that the rate of decomposition and the selectivity to cyclohexanone/cyclohexanol can be increased by increasing the basicity (pH) of the aqueous phase as compared to Example 5. The results are summarized in Table 1.

EXAMPLE 7

Example 6 was repeated except that the reaction temperature was increased to 147° C. and the reaction time was decreased to 5 minutes. Thus, 4.0 g of NaOH was dissolved in 40.0 g of degassed water. Furthermore, an amount of 40.00 g of a cyclohexane oxidate solution was used for injection in this experiment. The oxidate solution contained 10.931 mmol of cyclohexylhydroperoxide, 2.122 mmol of cyclohexanol, 1.702 mmol of cyclohexanone, 0.282 mmol of C1-C6 mono and dicarboxylic acids, 0.018 mmol of cyclohexyl esters of C1-C6 mono and dicarboxylic acids and 0.207 mmol of various non-acidic organic oxo-compounds. Otherwise, the reaction was carried in the absence of cobalt similarly as described above in Comparative Experiment A. After the reaction the following amount of components were found back in the two product fractions: 0.021 mmol of cyclohexylhydroperoxide, 4.419 mmol of cyclohexanol, 9.862 mmol of cyclohexanone, 0.450 mmol of C1-C6 mono and dicarboxylic acids, no cyclohexyl esters of C1-C6 mono and dicarboxylic acids and 0.367 mmol of various non-acidic organic oxo-compounds. This corresponds to 99.8% of conversion of cyclohexylperoxide with 95.7% selectivity to newly formed cyclohexanone and cyclohexanol with a molar ratio of 3.58. The selectivity to acids and undetected components was 1.4% and 1.5%, respectively. The example shows that in the presence of NaOH in the aqueous base the high selectivity to cyclohexanone/cyclohexanol and the high molar ratio of cyclohexanone to cyclohexanol can be maintained to as high as 147° C. by keeping the advantageously low base consumption as compared to Comparative Experiment A. The results are summarized in Table 1 feed solution comprising cyclohexylhydroperoxide with an aqueous base solution in the absence of a transition metal catalyst resulting in a mixture comprising (i) an aqueous phase and (ii) an organic phase comprising cyclohexanone and cyclohexanol, wherein the pH of the aqueous phase is higher than 13, measured at 25° C., and wherein said mixing is effected at a temperature lower than 170° C., and wherein the volume ratio of the aqueous phase to the organic phase is higher than 0.1.

2. Process according to claim 1, wherein said mixing is effected at a temperature lower than 150° C.

3. Process according to claim 1, wherein said mixing is effected at a temperature higher than 70° C.

4. Process according to claim 1, wherein said mixing is effected at a temperature higher than 100° C.

5. Process according to claim 1, wherein the pH of the aqueous phase is higher than 10, measured at 25° C.

6. Process according to claim 1, wherein the pH of the aqueous phase is higher than 13, measured at 25° C.

7. Process according to claim 1, wherein said aqueous base solution is an aqueous solution comprising dissolved base(s).

8. Process according to claim 1, wherein said aqueous base solution comprises carboxylic acid salts.

9. Process according to claim 1, wherein the process further comprises separating the aqueous phase from the organic phase.

10. Process according to claim 1, wherein the aqueous base solution comprises at least a portion of the aqueous phase obtained after said separating.

11. Process according to claim 1, wherein the process further comprises distilling the organic phase to obtain cyclohexanone.

12. Process for the preparation of cyclohexanone, said process comprising:
 (a) oxidizing cyclohexane with an oxygen-containing gas in the absence of a transition metal catalyst to obtain an oxidation reaction mixture comprising cyclohexylhydroperoxide, cyclohexane, cyclohexanol, cyclohexanone, acids, esters, low boiling compounds and high boiling compounds;
 (b) optionally, separating part of the cyclohexane from said oxidation reaction mixture;
 (c) optionally, neutralizing acids formed in the oxidation by treating the oxidation reaction mixture with an aqueous base solution;

TABLE 1

| | Temperature (° C.) | pH (at 25° C., theoretical) | Volume ratio aqueous phase/organic phase | Concentration of carboxylic acid salts in aqueous base solution (wt. %) | Reaction time (minutes) | Conversion (%) | Selectivity (%) | Molar ratio of cyclohexanone formed to cyclohexanol formed |
|---|---|---|---|---|---|---|---|---|
| Comp. Exp. A | 80 | 14.0 | 0.14 | 13.4 | 30 | 98.8 | 90.1 | 1.50 |
| Example 1 | 80 | 14.0 | 0.14 | 13.5 | 30 | 53.8 | 95.6 | 2.51 |
| Example 2 | 80 | 14.0 | 0.14 | — | 30 | 46.5 | 96.7 | 2.04 |
| Example 3 | 80 | 14.0 | 0.71 | 13.7 | 30 | 99.4 | 95.5 | 4.53 |
| Example 4 | 120 | 14.0 | 0.77 | — | 10 | 99.4 | 95.4 | 4.26 |
| Example 5 | 120 | 12.1 | 0.91 | — | 20 | 85.8 | 93.2 | 2.62 |
| Example 6 | 120 | 14.4 | 0.83 | — | 20 | 99.7 | 96.8 | 3.40 |
| Example 7 | 147 | 14.4 | 0.83 | — | 5 | 99.8 | 95.7 | 3.58 |

The invention claimed is:

1. Process for decomposing cyclohexylhydroperoxide into cyclohexanone, said process comprising mixing an organic (d) decomposing cyclohexylhydroperoxide obtained in (a) with the process according to claim 1 to obtain a mixture comprising (i) an aqueous phase and (ii) an organic phase comprising cyclohexane, cyclohexanone, cyclohexanol, low boiling compounds and high boiling compounds;

(e) separating the aqueous phase from the organic phase;

(f) optionally, recycling a portion of the separated aqueous phase to (c);

(g) distilling the organic phase to obtain cyclohexanone.

13. Process according to claim 12, wherein said distilling (g) comprises the following steps:
(g.1) separating cyclohexane from the organic phase,
(g.2) separating low boiling compounds from the organic phase,
(g.3) separating cyclohexanone from the organic phase, and
(g.4) separating cyclohexanol from the organic phase.

* * * * *